United States Patent [19]

Chlanda

[11] Patent Number: 5,049,250
[45] Date of Patent: Sep. 17, 1991

[54] ELECTRODIALYTIC TREATMENT OF AQUEOUS SOLUTIONS CONTAINING AMINO ACIDS

[75] Inventor: Frederick P. Chlanda, Rockaway, N.J.

[73] Assignee: Allied-Signal Inc., Morris Township, Morris County, N.J.

[21] Appl. No.: 393,165

[22] Filed: Aug. 14, 1989

[51] Int. Cl.$^5$ ............................................. B01D 13/02
[52] U.S. Cl. .............................. 204/182.4; 204/182.6; 204/131; 204/301
[58] Field of Search ............... 204/182.6, 182.3, 182.4, 204/131, 301

[56] References Cited

U.S. PATENT DOCUMENTS

| | | | |
|---|---|---|---|
| 4,238,306 | 12/1980 | Perry et al. | 204/182.6 |
| 4,238,307 | 12/1980 | Perry et al. | 204/180 P |
| 4,740,281 | 4/1988 | Chlanda et al. | 204/151 |
| 4,882,277 | 11/1989 | Czytko et al. | 204/182.4 |
| 4,885,247 | 12/1989 | Datta | 204/182.6 |
| 4,909,916 | 3/1990 | Koberstein et al. | 204/182.6 |

FOREIGN PATENT DOCUMENTS 786319  5/1963  Canada.

OTHER PUBLICATIONS

Journal of Applied Chemistry, vol. 8, "Electrodialysis Using ion-exchange Membranes II", Peers pp. 59–67, (1958).
Bull. Chem. Soc. Japan, vol. 36, No. 11, "Separation of Amino Acids with Ion exchange Membrane," Hara pp. 187–194 (1963).
Patent Abstracts of Japan vol. 13 No. 315 (C-619) (3663) 18 Jul. 1989 & JPA 1102049.
Patent Abstract of Japan vol. 4 No. 174 (C-33) (656) 2 Dec. 1980 & JPA 55116404.
Desalination vol. 68, Nos. 2,3 Mar. 1988 Elsevier Science Publishers.
BV (Amsterdam) NL KN MANI et al. "Aquatech Membrane Technology for Recovery of acid/base Values from Salt Streams" pp. 149–166.

Primary Examiner—John F. Niebling
Assistant Examiner—Arun S. Phasge
Attorney, Agent, or Firm—Karen A. Michaelsen

[57] ABSTRACT

The present invention is directed to a process for the separation of an aqueous solution of at least one amphoteric compound from an aqueous feed comprising the amphoteric compound including amino acids, and at least one salt. The process is conducted in an apparatus comprising at least one cell. The cell comprises at least one bipolar membrane each of which comprises a cation layer and an anion layer. Cells useful in the process of the present invention include arrangements with the bipolar membrane in combination with at least one cation membrane and/or at least one anion membrane.

19 Claims, 2 Drawing Sheets

ELECTRODIALYTIC TREATMENT OF AQUEOUS SOLUTIONS CONTAINING AMINO ACIDS

BACKGROUND OF THE INVENTION

The present invention relates to the treatment of ampholytes such as amino acids using an electrodialytic water-splitter. More particularly, the present invention is directed to the purification of ampholytes such as amino acids with the simultaneous production of acids and/or bases.

Reference is made to Condon and Meislich, Introduction To Organic Chemistry, published by Holt, Rinehart and Winston, Inc., pages 472-476 (New York, 1960), for a brief review relating to the properties of amino acids. Amino acids are amphoteric and ionized both as an acid and as a base in aqueous solution. For example, they can be titrated with a strong mineral acid (HCl) or alkali (NaOH) and form salts with either. Ionization with an acid results in formation of cationic species, while ionization with a base results in formation of an anionic form of the ampholyte. Condon discloses that during electrolysis of the solution of amino acid, the cationic form migrates toward the cathode, while the anionic form migrates toward the anode, each at a rate determined by the concentration and mobility. In strongly acidic solutions the cationic form dominates, and the net migration is toward the cathode, while in strongly basic solutions, the net migration is toward the anode.

At some intermediate pH characteristic for each amino acid, most of the acid is in the bipolar form and there is no net migration toward either electrode. The pH at which there is no net migration is known as the "isoelectric point". At the isoelectric point the fraction of amino acid in the bipolar form is a maximum, and its solubility a minimum. Advantage is taken of the differential rates of migration in a method of separating amino acids in proteins, known as electrophoresis.

Electrodialysis at the isoelectric point of amino acid/salt solutions will result in a separation of salt from the amino acid since the amino acid carries no net charge to cause it to migrate in the electric field. However, when the solution is not at the isoelectric point, the amino acid will have a net charge and will migrate through either the anion or cation permeable membranes, depending on the pH. It is not always convenient to adjust the pH to the isoelectric point, and in the case of mixtures of amino acids with widely differing isoelectric points, it may not be possible at all. For example, aspartic acid (ASP) $HOOCCH_2CH(NH_2)COOH$, and phenylalanine (PA) $C_6H_5CH_2CH(NH_2)COOH$, are found in the manufacture of the artificial sweetener aspartame and accumulate in a stream of high salt concentration. The isoelectric point of ASP is 2.98 and PA is 5.91, so a compromise would need to be reached on the proper pH for operation if salt were to be removed by electrodialysis. While PA is more valuable than ASP, ASP is also of substantial value and the loss of either amino acid to the salt would be undesirable.

The separation of amino acids from salts by electrodialysis is a well known process. The advantages of operating with acid on the anode side and base on the cathode side were realized as long ago as 1958, Peers, Electrodialysis Using Ion-exchange Membranes II. Demineralization of Solutions Containing Amino Acids, Journal of Applied Chemistry, 8, pp 59-67, January 1958. Peers discloses, beginning at page 65 the effect of anolyte and catholyte compositions. Peers uses a three-compartment electrodialysis unit wherein there is a center compartment and two side compartments separated from the center compartment by an anion exchange membrane and a cation exchange membrane. A solution of amino acid in salt is fed to the center compartment. Peers discloses that an acidic anolyte compartment results in the least amount of amino acid lost from solution after removal of 70% of sodium chloride present in the solutions. The behavior of the amino acid under circumstances of an acidic anolyte and a basic catholyte compartment is reviewed beginning at page 66 of Peers. Beginning at the first full paragraph at page 67, Peers considers the pH of the feed solution containing salt plus amino acid. Peers indicates that the bulk solution pH is not entirely unimportant if the amino acid concerned is strongly acidic or basic. Peers concludes that the separation of amino acid from sodium chloride has been shown to be improved by operating with relatively low current densities in a combination of acidic anolyte and alkaline catholyte.

Of interest is Smith et al., Electrolytic Desalting With Ion Exchange Membranes, Nature on page 83, Jan. 14, 1956. Also, of interest, is Hara, The Separation of Amino Acid With Ion Exchange Membrane, Bull. Chem. Soc. Japan, Volume 36, No. 11, pages 1373-1376 (1962). This paper discloses a separation of a mixture of amino acids obtained from the hydrolysis of gluten carried out by electrodialysis.

Also, of interest is Hara, Permeability of Acidic Amino Acid Through Anion Exchange Membrane, Bull. Chem. Soc Japan, Volume 36, No. 2, pages 187-194 (1963).

Electrodialytic water-splitting in a two-compartment cell is well known. For example, U.S. Pat. No. 4,391,680 discloses the generation of strongly acidified sodium chloride and aqueous sodium hydroxide by two-compartment water-splitting of aqueous sodium chloride. Three-compartment electrodialytic water-splitters are known in the art. They are disclosed to be comprised of alternating bipolar, anion and cation exchange membranes, thereby forming alternating acid, salt and base compartments. U.S. Ser. No. 235,562 discloses three compartment electrodialytic water-splitters. U.S. Pat. No. 4,740,281 discloses the recovery of acids from materials comprising acid and salt using an electrodialysis apparatus to concentrate the acid followed by the use of an electrodialytic three-compartment water-splitter to separate the acid from the salt.

U.S. Pat. No. 4,608,141 discloses a multi-chamber two-compartment electrodialytic water-splitter and a method for using the same for the basification of aqueous soluble salts. U.S. Pat. No. 4,536,269 discloses a multi-chamber two-compartment electrodialytic water-splitter and a method for using the same for the acidification of aqueous soluble salts. These two patents review the use of two-compartment electrodialytic water-splitters and their use to treat salts.

The staging of two conventional two-compartment electrodialytic water-splitters, whereby the base solution is withdrawn from the base compartment of one two-compartment water-splitter, and is fed through the base compartment of the second two-compartment water splitter, is known. In an attempt to increase the efficiency of bipolar membranes, U.S. Pat. No. 3,111,472 (Oda, et al.) discloses disposing a microporous water permeable cation or neutral membrane in the acid and/or base compartments of the three compartment electrodialytic water-splitter.

Bipolar membranes have been known to be useful for the process of electrodialytic water-splitting to generate an acid and a base for many years (Oda et al., U.S. Pat. No. 2,289,095, Chlanda et al., U.S. Pat. No. 3,787,304, Jenczewski et al., U.S. Pat. No. 4,552,635). Their use in various cell configurations has been reported (Oda et al., Japanese 2023 ('58) reported in Chemical Abstracts 53:11070b., U.S. Pat. No. 4,536,269 and U.S. Pat. No. 4,608,141).

None of the above references disclose separating a amphoteric compound from a salt solution using a bipolar membrane.

SUMMARY OF THE INVENTION

The present invention is directed to a process for the separation of an aqueous solution of at least one amphoteric compound from an aqueous feed comprising the amphoteric compound and at least one salt. The amphoteric compound includes amino acids. The salt comprises a salt anion and a salt cation.

The process is conducted in an apparatus comprising at least one cell. The cell comprises at least one bipolar membrane each of which comprises a cation layer and an anion layer. Cells useful in the process of the present invention include arrangements with the bipolar membrane in combination with at least one cation membrane and/or at least one anion membrane.

In a specific and preferred embodiment, there is at least one cation membrane and at least one anion membrane. There is a base compartment between the anion layer of the bipolar membrane and the cation membrane and a salt compartment between the cation membrane and the anion membrane. There is an acid compartment on the side of the anion membrane opposite the salt compartment.

Using this configuration the method of the present invention comprises supplying the feed which comprises at least one amphoteric compound and at least one salt to the salt compartment, and a liquid comprising water to the acid and base compartments. A direct current is applied to the cell to force the salt cations to migrate to the base compartment to form base, and the salt anions to migrate to the acid compartment to form acid. The amphoteric compound remains in the salt compartment. Aqueous acid solution is recovered from the acid compartment. Aqueous base solution is recovered from the base compartment. An aqueous solution of the amphoteric compound is recovered from the salt compartment, less the salt which was transported to the acid and base compartments.

In an alternate embodiment of the present invention, the cell comprises a bipolar membrane as recited above. There is at least one anion membrane. There is a salt compartment defined between the anion layer and the anion membrane and an acid compartment on the side of the anion membrane opposite the salt compartment. Using this configuration, the process comprises supplying the feed which comprises at least one amphoteric compound and at least one salt to the salt compartment and a liquid comprising water to the acid compartment. A direct current is applied to the cell to force the salt anions to migrate to the acid compartment to form acid. The salt cations and amphoteric compound remain in the salt compartment. Acid is recovered from the acid compartment. An aqueous solution of basified amphoteric compound is recovered from the salt compartment, less the salt which formed the acid.

In another configuration, the unit cell comprises the bipolar membrane as recited above and at least one cation membrane. A base compartment is defined between the anion layer and the cation membrane. There is at least one salt compartment on the side of the cation membrane opposite the base compartment. Using this configuration, the process comprises the steps of supplying the feed to the salt compartment and a liquid comprising water to the base compartment. A direct current is applied to the cell to force the salt cations to migrate to the base compartment to form base. Salt anions and the amphoteric compound remain in the salt compartment. Base is recovered from the base compartment and an aqueous solution of acidified amphoteric compound is recovered from the salt compartment, less the salt which formed the base.

In yet another embodiment, the cell comprises two bipolar membranes and at least one cation membrane and at least one anion membrane. The membranes are configured so that there is a first salt compartment between the cation layer of the first bipolar membrane and the cation membrane, a base compartment between the cation membrane and the anion layer of the second bipolar membrane, an acid compartment formed by the cation layer of the second bipolar membrane and the anion membrane and a second salt compartment on the side of the anion membrane opposite the acid compartment. Using this configuration, the process comprises the steps of supplying the feed to the first and second salt compartments and a liquid comprising water is supplied to the acid and base compartments. A direct current is applied to the cell to force salt cations to migrate from the first salt compartment to the base compartment to form base, and the salt anions to migrate from the second salt compartment to the acid compartment to form acid. Amphoteric compound and salt anions remain in the first salt compartment and amphoteric compound and salt cations remain in the second salt compartment. Acid is recovered from the acid compartment and base is recovered from the base compartment. An aqueous solution of acidified amphoteric compound is recovered from the first salt compartment, less salt which formed base, and basified amphoteric compound is recovered from the second salt compartment less salt which formed acid.

Useful amphoteric compounds comprise at least one amino acid. The process of the present invention is particularly useful wherein the amino acid is a mixture of aspartic acid and phenylalanine. The salt is typically sodium chloride. A mixture of aspartic acid, phenylalanine and sodium chloride is a by-product solution formed during the manufacture of the artificial sweetener aspartame.

The use of the bipolar membrane results in formation of acid in the acid compartment and base in the base compartment. The presence of the acid in the base prevents the migration of the amphoteric compounds out of the salt compartment, thereby permitting the salt to be removed while the amphoteric compound remains behind in a more purified state. The use of the bipolar membrane in these particular cells makes the process of purification substantially independent of the pH of the feed solution. Although the advantages of operating with acid on the anode side, and base on the cathode side, using monopolar membranes were realized as long ago as 1958 by Peers, there was no disclosures of the advantages using a bipolar membrane. In such operation, positively charged amino acid in the de-salting compartment, present in significant amounts below the isoelectric point moves toward the cathode under the influence of the electric potential gradient. However, there is some leakage of hydroxyl ions across the cation membrane. As the positively charged amino acid approaches or passes through the cation membrane the proton giving the positive charge reacts with the hydroxide. The amphoteric amino acid ion becomes neutral and its motion is relatively unaffected by the electric potential. Further migration toward the cation could result in further reaction of the proton on the neutral amino acid with an additional hydroxyl ion. This could result in a negative charge on the amino acid and so the electric potential gradient would then tend to move the amino acid back to the salt compartment. The opposite situation results if a negatively charged amino acid begins to move toward the anode.

The use of bipolar membranes thereby maintains the necessary acidity and basicity. Additionally, the bipolar membranes result in the production of acid and base product which themselves have value and can be recycled. The bipolar membrane is a more efficient means of supplying the hydrogen and hydroxyl ions than electrodes, since the bipolar membranes consume less electricity and do not require external electrical connection to function. In addition, the bipolar membranes avoid problems of oxidation/reduction of the amphoteric compound or the acid and base products which can occur when the acid and base are supplied by electrode reactions. For example, if the salt is a chloride, chlorine would be formed at the anode if electrodes replaced the bipolar membranes. Because of its high reactivity and toxicity, special precautions must be taken in handling the product and only oxidation resistant membranes can be used. These considerations add substantially to the cost and complexity of the process.

The use of the bipolar membrane provides the additional advantage of being able to use a multiple of cells from one to several hundred, i.e., 1 to 500, typically from 20 to 200, and more usually, from 20 to 100 between a single set of electrodes Prior art such as Peers describes a single de-salting compartment between a single set of electrodes.

DETAILED DESCRIPTION OF THE INVENTION

Figure 1:
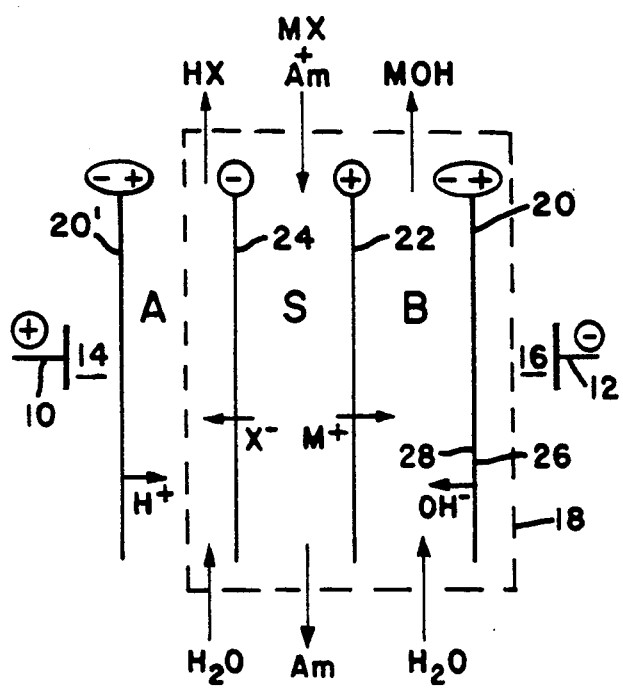
FIG. 1 schematically illustrates an electrodialysis unit for separating amphoteric compounds from an aqueous solution containing amphoteric compounds and a water soluble salt.

The present invention will be understood by those skilled in the art by reference to the accompanying drawings.

The present invention is directed to a method for treating aqueous solutions comprising at least one amphoteric compound and at least one water soluble salt. This solution is treated to produce a separate aqueous solution containing the amphoteric compound or alternately, a basic salt or acidic salt of the amphoteric compound. In accordance with the method of the present invention the solution of amphoteric compound and salt and the aqueous stream can be treated to result in higher concentrations of the amphoteric compound.

The process of the present invention is conducted in an apparatus comprising at least one bipolar membrane. A bipolar membrane is a membrane comprising a cation layer and an anion layer, the bipolar membrane is used in combination with at least one cation membrane and/or at least one anion membrane to form a cell. Each cell is a complete unit which can be used to accomplish the process of the present invention. Preferably, there are a plurality of repeating cells. The various bipolar, and cation and/or anion membranes are arranged between a pair of electrodes which can be used to apply an electric potential difference causing a direct current to flow. There are spaces or compartments between adjacent membranes. In accordance with the present invention three types of compartments are formed. There is a salt compartment (S) into which the aqueous solution comprising the amphoteric compound and water soluble salt is fed. There is an acid compartment (A) in which acid is formed and an acid product stream removed. There is a basic compartment (B) in which a base is formed and an aqueous stream containing the base is removed. There is a anolyte compartment adjacent to the anode and a catholyte compartment adjacent to the cathode.

Briefly, the aqueous solution of amphoteric compound and water soluble salt is fed to the salt compartment of a cell of the present invention. Adjacent to the salt compartment are an acid compartment on one side and/or a base compartment on the opposite side. A direct current is applied across the electrodes. The spaces between the membranes, which form compartments, are substantially closed except for inlets and outlets. Anion membranes permit anions, ions with a negative charge, to be transported while preventing the passage of cations. The cation membranes are designed to permit the passage of cations, ions with a positive charge, typically cations of metals, while preventing the passage of anions. The selectivity of anion and cation membranes is not perfect, however. There is always some leakage of anions, e.g., hydroxyl ion, across the cation membrane and some leakage of cations, e.g., hydrogen ions, across the anion membrane.

Positively charged amphoteric compounds, for example, a protonated amino acid, in the salt compartment move toward the cathode under the influence of the electrical potential gradient. As the positively charged amino acid approaches or passes through the cation membrane, the proton giving the positive charge reacts with the hydroxide. The ion becomes neutral and its motion is relatively unaffected by the electrical potential. Further migration toward the cathode could result in further reaction of the carboxylic proton on the neutral amino acid with an additional hydroxyl ion. This results in a net negative charge of the amino acid so that the electric potential gradient would tend to move the amino acid back to the de-salting compartment. Correspondingly, the opposite situation results if negatively charged amino acid begins to move toward the anode. Accordingly, by this principal, it has been found that when dealing with amphoteric compounds the amphoteric compound tends to remain in the salt compartment when an acid solution is maintained in the compartment adjacent to the salt compartment on the anode side and a base solution is maintained in the compartment adjacent to the salt compartment on the cathode side. In accordance with the process of the present invention, the isoelectric point of the amphoteric compounds need not be maintained to keep the amphoteric compound in the salt compartment. This advantage permits the treatment of mixtures of at least two amphoteric compounds having widely varying isoelectric points. Since the effectiveness of retaining the amphoteric compound in the salt compartment depends on the transport of hydrogen ions across the anion membrane or hydroxyl ions across the cation membrane, these parameters can be adjusted by means such as changing solution concentrations, current density, temperature, membrane ion exchange capacity, water content (swelling) and thickness, in order to optimize the process.

The present invention has been found to be particularly useful where the amphoteric compounds are amino acids. Such amino acids include, but are not limited to, glycine, alanine, valine, leucine, isoleucine, serine, threonine, cystine, methionine, proline, hydroxyproline, phenylalanine, tyrosine, tryptophan, aspartic acid, glutamic acid, arginine, lysine, sarcosine, and histidine, and mixtures thereof.

Salts from which the amphoteric compounds can be separated are water soluble salts, including, but not limited to, salts of cations which include mono, di and trivalent metallic and non-metallic ions including ammonium. The anions of the salt include monovalent anion, such as halides, divalent anions such as sulfates, and trivalent anions such as phosphates and mixtures thereof. Typical salts include, but are not limited to, alakli metal halides, such as sodium chloride and potassium chloride; ammonium halides, such as, ammonium chloride; and sulfates, nitrates and phosphates, such as sodium sulfate, sodium nitrate, ammonium nitrate, sodium phosphate, potassium fluoride, and mixtures thereof The aqueous solutions of the amphoteric compounds and water soluble salts are typically by-products of commercial reactions or fermentation processes. A waste stream which can be treated is from a process to produce the artificial sweetener aspartame. Waste streams from such a process include ammonium chloride and/or sodium chloride, L-aspartic acid and L-phenylalanine.

Specific and preferred embodiments of the process of the present invention can be accomplished in accordance with the apparatus illustrated in FIGS. 1-4.

Each of FIGS. 1-4 comprise an anode 10 and a cathode 12. In each of the preferred embodiments illustrated in FIGS. 1-4 there is at least one cell which is useful to eliminate salt or a component of the salt from a solution of amphoteric compound and water soluble salt. This is accomplished by the use of the specific cell structure when a direct current is applied across the cell by the electrodes, anode 10 and cathode 12. There is an anolyte compartment 14 between anode 12 and the cells and a catholyte compartment 16 between the cathode 12 and the cells. An aqueous based anolyte and catholyte solution are fed through inlets and outlets in the anolyte compartment 14 and catholyte 16.

There are preferably a plurality of cells in accordance with the apparatus used in the process of the present invention. There can be from 1 to 500 or more such cells. Typically, there is from 20 to about 200, and preferably, from 50 to 200 cells. In the embodiments illustrated in FIGS. 1-4, each repeating unit cell is surrounded by a dotted line. Referring to the embodiment illustrated in FIG. 1, each cell 18 comprises a bipolar membrane 20, a cation membrane 22 and an anion membrane 24. The cell is located between anode 10 and cathode 12. The cation layer 26 of the bipolar membrane 20 faces cathode 12 and the anion layer 28 faces anode 10. Cation membrane 22 is adjacent to anion layer 28 of bipolar membrane 20. There is a space between bipolar membrane 20 and cation membrane 22. This space is the base compartment B. The base compartment is substantially closed except for inlets and outlets. Adjacent to cation membrane 22 on the side opposite bipolar membrane 20 is anion membrane 24. There is a space between cation membrane 22 and anion membrane 24. This space forms salt compartment S and is substantially closed except for inlets and outlets. There is an acid compartment A on the side of the anion membrane 24 opposite the salt compartment S. In the embodiment illustrated in FIG. 1, the acid compartment A is shown as the space between anion membrane 24 and bipolar membrane 20' of the next adjacent cell. As with the salt and base compartments, the acid compartment is substantially closed except for inlets and outlets.

In accordance with the process of the present invention an aqueous feed stream comprising at least one water soluble salt (MX, with $M^+$ being the salt cation and $X^-$ being the salt anion) and at least one amphoteric compound (Am) is fed to salt compartment S. Aqueous streams ($H_2O$) are fed to acid compartment A and base compartment B. Aqueous streams are also fed to anolyte compartment 14 and catholyte compartment 16. The aqueous stream fed to the acid compartment, to the anolyte and catholyte compartments, as well as the acid and base compartments, primarily comprise water, but can be dilute salt, acid or base solutions. For convenience, the acid and base compartments are shown being fed with $H_2O$. A potential is applied across electrodes anode 10 and cathode 12 causing a direct current to flow. Cations from the salt migrate toward cathode 12 and anions from the salt migrate toward anode 10. Water is split at bipolar membranes 20 and 20', resulting in hydroxyl ions entering base compartment B and hydrogen ions entering acid compartment A. The cations combine with the hydroxyl ions to form base which is removed from the base compartment as MOH and the hydrogen ions combined with the anions to be removed as an aqueous solution of acid shown as HX from the acid compartment. For the reasons discussed above, the amphoteric compounds remain substantially in the salt compartment S. In FIG. 1 the amphoteric compounds are shown being removed as Am. The amphoteric compounds are removed in an aqueous solution. The apparatus used in FIG. 1 can treat the feed solution to remove substantially all of the salt or some of the salt so that the solution is more concentrated with respect to the amphoteric compound. In addition, because of water transport with the salt to the acid and base, the absolute concentration of the amphoteric compound may be increased.

Figure 2:
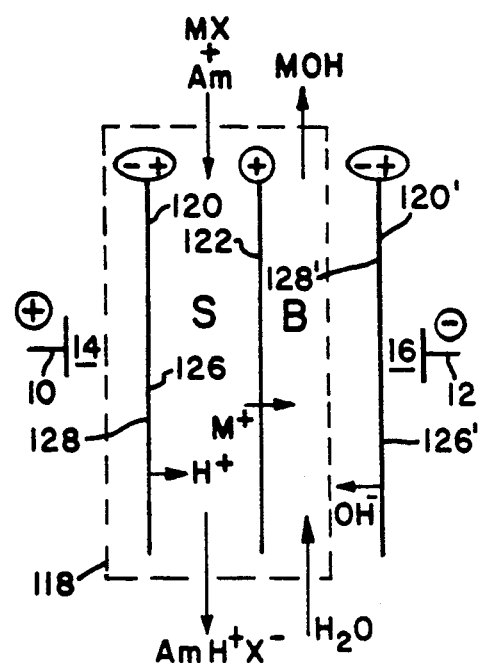
FIG. 2 schematically illustrates an electrodialysis unit for treating an aqueous solution comprising an amphoteric compound and a water soluble salt to produce an acidic salt of the amphoteric compound separated from the base.

An embodiment of the process of the present invention using the apparatus of FIG. 2 contains analagous components to those reviewed with regard to FIG. 1, and reference is made to the above description regarding common features.

In accordance with the process of FIG. 2, an aqueous feed comprising a water soluble salt and at least one amphoteric compound is treated to produce an acidic amphoteric compound A cell in accordance with FIG. 2 comprises a bipolar membrane 120 adjacent to a cation membrane 122. The space between the cation membrane 122 and the cation layer of the bipolar membrane 120 is the salt compartment S. The salt compartment is substantially closed except for inlets and outlets. There is a base compartment B on the side of the cation membrane 122 opposite the salt compartment. Typically, this space is between the cation membrane 122 and the anion layer 128' of the next bipolar membrane 120'. As with the other compartments, the base compartment B is substantially closed except for inlets and outlets.

In accordance with the process of the present invention an aqueous solution comprising at least one amphoteric compound and at least one water soluble salt is fed into the salt compartment. Substantially aqueous solution is fed into the base compartment and anolyte and catholyte solutions fed to the anolyte 14 and catholyte 16 compartments. A direct current is applied to the cell between the electrodes, anode 10 and cathode 12. The electric field causes the salt cations $M^+$ to migrate across cation membrane 122. Water is split at the bipolar membranes 120 and 120'. Hydrogen ion enters the salt compartment S from the cation surface 126 of bipolar membrane 120. Hydroxyl ion enters the base compartment B from bipolar membrane 120' at anion surface 128'. An aqueous basic solution formed in base compartment B is removed as MOH. The salt anions $X^-$ remain in the salt compartment S. These combine with the amphoteric compound, and the hydrogen ion to form an acidic compound shown as $AmH^+X^-$. This is removed in an aqueous product stream. As with the embodiment of FIG. 1, the apparatus can be operated to remove substantially all of the metal cations $M^+$ from the salt compartment, leaving the acidic amphoteric compound, provided that MX and Am are present in equivalent amounts in the feed. If excess MX is present, substantial amounts of HX can be introduced into the product along with $AmH^+X^-$ provided $X^-$ is the anion of a weak acid. For strong acids, the amount of HX which can be formed with high efficiency will be limited by $H^+$ transport across the cation membrane. When more amphoteric compound is present in the feed than salt, all of the salt cations will be removed before conversion to $AmH^+X^-$ is complete and the resulting product will contain Am in addition to $AmH^+X^-$.

Figure 3:
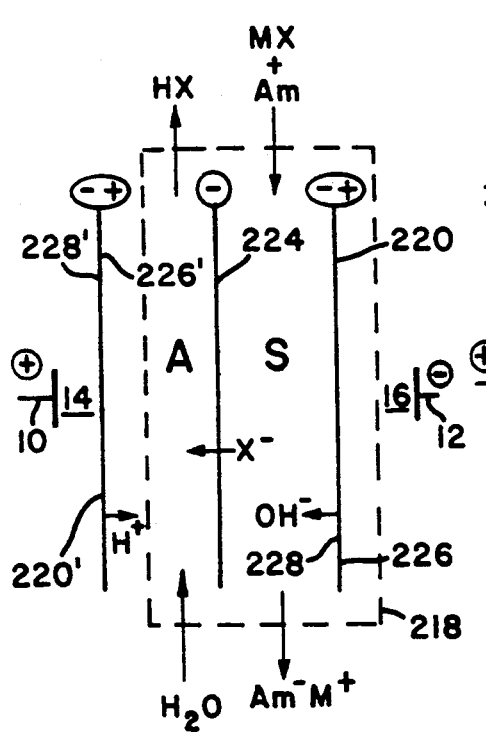
FIG. 3 schematically illustrates an electrodialysis unit for treating an aqueous solution containing an amphoteric compound and a water soluble salt to produce an acidic amphoteric compound separated from an acid.

FIG. 3 schematically illustrates an apparatus useful for a further embodiment of the present invention. Initially, reference is made to the above description regarding the embodiment of FIG. 1. The cell 218 of FIG. 3 comprises a salt compartment and an acid compartment. There is a bipolar membrane 220 comprising a cation layer 226 and anion layer 228. Adjacent to the bipolar membrane 220 is an anion membrane 224. Salt compartment S is defined as the space between the anion surface 228 of bipolar membrane 220 and the anion membrane 224. The salt compartment is substantially closed except for inlets and outlets. There is an acid compartment A on the side of the anion membrane 224 opposite the salt compartment S. In the embodiment illustrated in FIG. 3 the acid compartment A is located between anion membrane 224 and the cation surface 226' of bipolar membrane 220' from the next cell or part thereof. The acid compartment is substantially closed except for inlets and outlets.

In accordance with the process of the present invention an aqueous feed stream comprising at least one amphoteric compound (Am) and at least one water soluble salt (MX) is fed to the salt compartment S. A water based feed stream is fed to the acid compartment as well as anolyte and catholyte compartments. A potential is applied across the cells by electrodes, anode 10 and cathode 12 causing a direct current to flow. The direct current results in anions $X^-$ from the salt migrating toward the anode 10 across anion membrane 224. Water is split at the bipolar membranes 220 and 220'. Hydroxyl ions enter the salt compartment from the anion surface 228 of bipolar membrane 220. Hydrogen ions enter the acid compartment A from the on surface 226' of bipolar membrane 220'. The hydrogen ions combine with the anions $X^-$ to form an aqueous solution of acid HX. This aqueous solution is removed in an acid stream HX. When an equivalent amount of the amphoteric compound or more is present the process can be operated until substantially all of the anion $X^-$ is transferred to the acid compartment. The product stream comprises a basic amphoteric compound indicated as $Am^-M^+$. If $M^+$ is the cation of a weak base, e.g., $M^+=NH_4^+$, then if MX is present in excess in the feed, substantial amounts of base MOH may be produced in the product in addition to the $Am^-M^+$.

Figure 4:
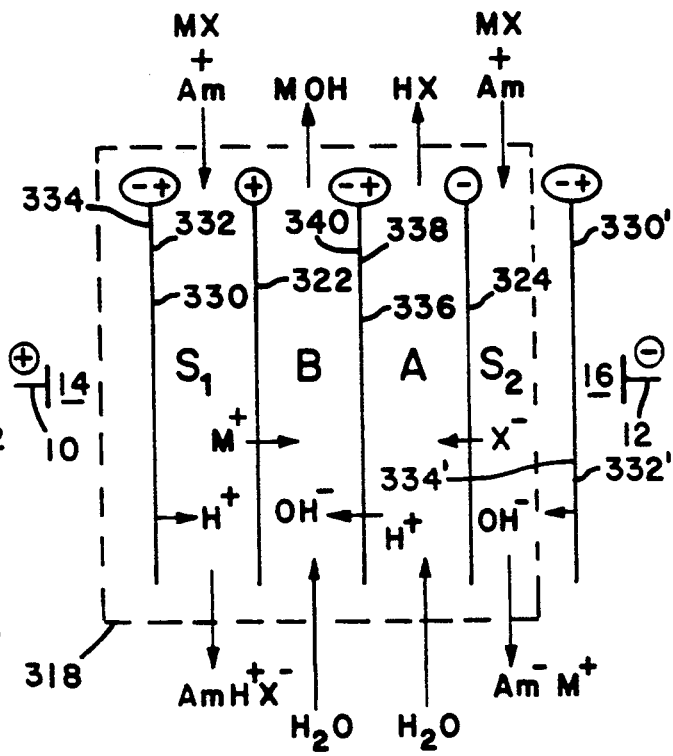
FIG. 4 schematically illustrates an electrodialysis unit for simultaneously producing an acidic and a basic salt of an amphoteric compound and separating out acid and base.

FIG. 4 illustrates a schematic diagram of an apparatus in yet a further embodiment of the present invention. In this embodiment each cell 318 comprises a first bipolar membrane 330 having a first cation layer 332 and a first anion layer 334. There is a second bipolar membrane 336 having a second cation layer 338 and a second anion layer 340. There is a cation membrane 322 located between the cation layer 338 of the first bipolar membrane 330 and the anion layer 340 of the second bipolar membrane 336. The space between the second anion layer 340 and the cation membrane 322 forms the base compartment (B). The base compartment is substantially closed except for inlets and outlets. The space between the cation layer 332 of the first bipolar membrane 330 and the side of the cation membrane 322 opposite the base compartment defines the first salt compartment ($S_1$). The salt compartment is substantially enclosed except for inlets and outlets. There is an anion membrane 324 opposite the cation layer 338 of the second bipolar membrane 336. The space between the cation layer 338 and the anion membrane is the acid compartment (A) which is substantially closed except for inlets and outlets. On the side of the anion membrane opposite the second bipolar membrane 336 is located a second salt compartment ($S_2$). In the embodiment illustrated in FIG. 4, this is bounded on the side opposite the anion membrane 324 by a first bipolar membrane 330' from an adjacent cell or part thereof.

In operation, this cell can be used to produce simultaneously acid, base, an acidic amphoteric compound and a basic amphoteric compound. In accordance with the process of the present invention, an aqueous solution comprising at least one amphoteric compound and at least one aqueous salt is fed to each salt compartment $S_1$ and $S_2$. An aqueous solution comprising substantially water is fed to the acid compartment A, the base compartment B, and the anolyte and catholyte compartments 14 and 16. A direct current is applied across the cell by electrodes, anode 10 and cathode 12. At the first bipolar membrane 330 hydrogen ions are formed and enter salt compartment $S_1$. The potential gradient causes salt cations $M^+$ to migrate toward the cathode 12. The salt cations leave the first salt compartment $S_1$ and cross cation membrane 322 into base compartment B. The second bipolar membrane splits water and hydroxyl ions migrate from the anion layer of the second bipolar membrane into the base compartment. The hydroxyl ions combine with the salt cations to form a base. Hydrogen ions formed at the second bipolar membrane migrate from the cation layer of the second bipolar membrane into the acid compartment. Salt anions in the second salt compartment $S_2$ migrate across anion membrane 324 into the acid compartment A. An aqueous acidic solution HX is then formed. Hydroxyl ions from the adjacent first bipolar membrane 330' enter into salt compartment $S_2$ from the anion layer 334' of the adjacent first bipolar membrane 330', thereby forming a basic amphoteric salt in the second salt compartment $S_2$. During operation the acidic amphoteric salt is removed from $S_1$ as product stream indicated by $AmH^+ X^-$, and the basic amphoteric salt stream is removed from S as product stream indicated by $Am^- M^+$. An aqueous basic stream containing the base formed MOH and an aqueous acid stream containing the acid formed HX are removed respectively from the base compartment and acid compartment.

The process in accordance with the apparatus illustrated in FIG. 4 can be conducted until all of the cations are removed from the solution in first salt compartments $S_1$ and al of the anions from the salt are removed from the second salt compartments $S_2$.

Figure 5:
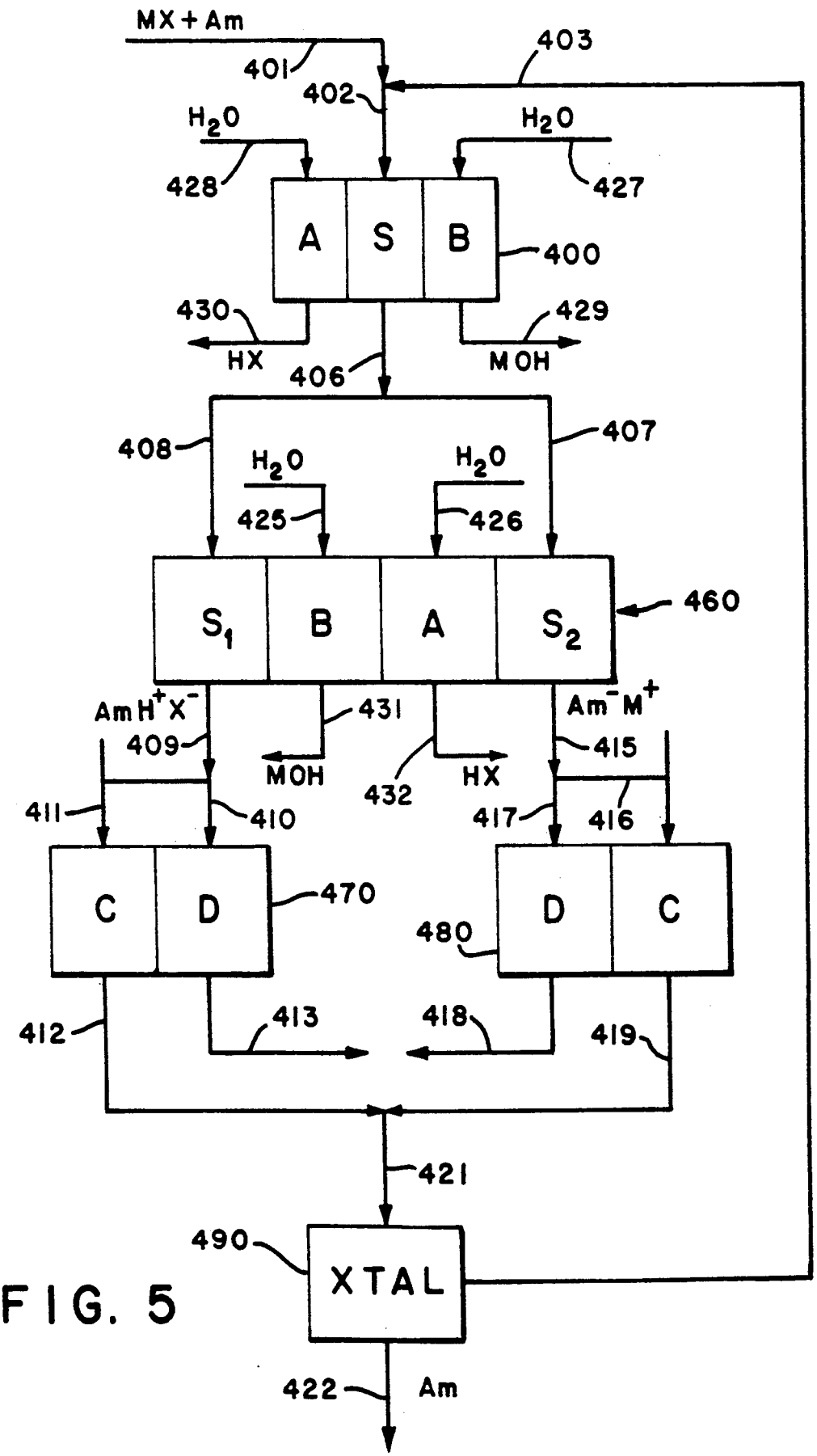
FIG. 5 illustrates a use in combination of the embodiment shown in FIG. 1 to concentrate an aqueous solution, an amphoteric compound and a salt. The concentrated solution is fed to a second electrodialysis unit of the type illustrated in FIG. 4. The acidic and basic amphoteric compounds are then concentrated and further treated.

FIG. 5 illustrates a method of concentrating and purifying amphoteric compounds, particularly amino acids, such as a mixture of aspartic acid and phenylalanine, in an aqueous waste stream resulting from a process to make the artificial sweetener aspartame. Initially, an aqueous stream containing at least one salt MX, such as sodium chloride, and additionally, at least one amphoteric compound, such as glycine, are fed to the salt compartment of an electrodialysis apparatus 400. This apparatus is identical to that illustrated in FIG. 1. The electrodialysis apparatus 400 is used to concentrate the amphoteric compounds relative to the salt compounds. The concentration of salt is reduced with aqueous streams of acid (HX) and base (MOH) being removed. The salt depleted stream 406 is then fed to a second electrodialysis apparatus 460, which is identical to the apparatus illustrated in FIG. 4 and described above. Optionally, separate units as shown in FIGS. 2 and 3 could be substituted for the combined apparatus shown in FIG. 4. Streams of aqueous solutions of acidic amphoteric salts 409 and basic amphoteric salts 415, are removed in product streams $AmH^+X^-$ and $Am^-M^+$, respectively. These streams are respectively sent to acidic salt concentrator 470 and basic salt concentrator 480. The acidic and basic salt concentrators are known in the art. Useful concentrators can be electrodialytic stacks or alternately, reverse osmosis units, both well known in the art. In the embodiment illustrated in FIG. 5, the basic amphoteric salt stream 415 is fed to the diluting compartment D of electrodialysis unit 480 and the acidic amphoteric salt stream 409 is fed to the diluting compartment D of electrodialysis unit 470. An aqueous stream is supplied to concentrating compartments of the respective electrodialysis unit, via lines 411 and 417, respectively. Although these streams are conveniently derived from the basic and acid amphoteric salt products from apparatus 460, separate streams comprising water may be used. Alternatively, the streams are omitted and the aqueous streams from the concentrate compartments (C) consist only of the materials transported in the concentrators. Both dilute streams are removed from the diluting compartment D as dilute amphoteric acidic salt stream 413 and dilute amphoteric basic stream 418. These streams which have had most of the amphoteric compound removed may be recycled, further concentrated by e.g., evaporation or reverse osmosis, or disposed of. The concentrated amphoteric acid stream 412, the concentrated amphoteric base stream 419 can be further treated. In the embodiment illustrated in FIG. 5, they can be combined and treated in crystallizer 490. The amphoteric salts mixed together can be precipitated as the neutral amphoteric compound and the mother liquor recycled or further treated in electrodialysis units, such as FIG. 1.

The feed streams can have amphoteric compound concentrations in a range of from 0.01M and preferably 0.1M, up to concentrations of 2M or more. The concentration of the product will usually be higher than the concentration of the feed, but may be equal or lower especially when the feed concentration is high. In this respect it may be necessary to dilute the feed stream or increase its temperature to prevent the precipitation of the neutral amphoteric compound in the apparatus. The efficiency of a system of the type shown in FIG. 1 depends on the selectivity of the cation and anion membranes. Preferably, the concentration of amphoteric compound in the feed is 0.5M to 2M, and most preferably 0.5M to the saturation limit of the neutral amphoteric compound. The salt can be at concentrations up to saturation, preferably from 0.5 molar to saturation concentration, and typically 0.1 molar or more.

Preferably, the resulting product streams will have no more than 1/10 times and preferably no more than 1/100 times the salt concentration as the original feed stream.

Useful operating temperatures of from 0° C. and 100° C. are possible if the stability of the membranes and the solubility and stability of the solution constituents permit. Generally, membrane life is longer at lower temperatures and power consumption will be lower at higher temperatures. Preferred operating temperatures are between 25° and 60° C. and more preferably, from 35° to 50° C.

Examples of bipolar membranes which are particularly useful include those described in U.S. Pat. No. 2,829,095 to Oda, et a. (which has reference to water-splitting generally), in U.S. Pat. No. 4,024,043 (which describes a single film bipolar membrane), and in U.S. Pat. No. 4,116,889 (which describes a cast bipolar membrane and is most preferred). In addition to bipolar membranes, structures which function as bipolar membranes, such as those described in U.S. Pat. No. 3,704,218, may also be employed.

The cation membranes employed in both the base purification unit and the three-compartment electrodialytic water-splitter may be moderately acidic (e.g., phosphonic group-containing) or strongly acidic (e.g., sulfonic group-containing) cation permselective membranes having a low resistance at the pH at which they are employed. Particularly useful cation membranes are DuPont's Nafion 110 and 324 cation membranes. More preferably, the cation membranes are of the composition and construction as disclosed in U.S. Pat. No. 4,738,764 to Chlanda, et al.

The anion membranes used in the three-compartment electrodialytic water-splitter are strongly, mildly, or weakly basic anion permselective membranes. Usable membranes, are, for example, commercially available from Ionics, Inc., Watertown, Mass. (sold as Ionics 204-UZL-386 anion membrane), or from Asahi Glass Co. (sold under the trade name Selemion AMV, ASV, or AAV anion permselective membranes).

The electrodialytic water-splitter can be operated in a batch mode, a continuous mode, or variations thereof. Product solutions or portions thereof (e.g., when using a feed and bleed apportionment operation) may be recycled for further concentration. Moreover, it should be evident that mechanisms for serial feed through similar compartments (not shown) may be employed. These and other modifications, changes and alterations to the design of the water-splitter will not affect the scope of the invention and will be obvious to those of ordinary skill.

In electrodialysis and related processes, generally the flow rate through the stack is higher than the input rate of fresh feed. The stack is operated in a recycle mode with the recycle feed being obtained from a recycle reservoir. In this way, one can determine and adjust the net input rate to obtain the desired composition changes for the entire system, even though the stack may be small. Feed to each recycle loop of the system and product removal may be made continuously (steady state operation) or periodically (batch operation).

The current passed through the apparatus in conventional fashion is direct current of a voltage dictated by design and performance characteristics readily apparent to the skilled artisan and/or determined by routine experimentation. Current densities between 25 and 300 amps per square foot (between 28 and 330 milliamps per square centimeter) are preferred; and current densities between 50 and 150 amps per square foot (between 55 and 165 milliamps per square centimeter) are more preferred. Higher or lower current densities can be used for certain specific applications.

In general, electrodialysis is performed in a "stack", a filter press like arrangement. The stack consists of a means of clamping and at each end of the stack, backup plates for the electrodes, the electrodes themselves to which elecrical connection is made for the purpose of introduction of direct current, compartments and membranes next to the electrodes to isolate them from the process streams, and interposed between these two ends, a series of repeating units (unit cells), formed of membranes and thin spacers. The stack may also contain additional structures such as periodic thicker spacers (spacer plates) which permit the introduction and removal of the process streams to external piping. Most cells are internally manifolded, i.e., holes punched through the spacer and the periphery of the membrane align to conduct solution from one end of the stack to the other or at least between spacer plates. The spacer is a thin flat sheet, the cental area of which is at least partially open. The spacer acts as a gasket around the periphery of the active area of the membrane so that two adjacent membranes and a spacer form a compartment. Solution is conducted to this compartment by a passage (port) in the spacer leading from a manifold to the compartment and removed by a corrresponding passage to another manifold. Part of the spacer may be a screen which partially fills the compartment and helps to keep the membranes separated and promotes good flow throughout the compartment.

The components of a unit cell, such as shown in FIG. 1, of this invention would consist of (beginning at the anode end) an acid compartment spacer, a anion membrane, a salt compartment spacer, a cation membrane a base compartment spacer and a bipolar membrane.

The following examples illustrate the practice of the present invention. The examples should not be construed as limiting the invention to anything less than that which is disclosed or that which would have been obvious to one of ordinary skill in the art therefrom. Two examples were conducted based on two samples of waste solution from a production process for aspartame.

The first solution contained a high concentration of ammonium chloride. This first solution reportedly contained 1.2% by weight of L-aspartic acid and 1.65% of L-phenylalanine. The first stream containing ammonium chloride was analyzed and found to be 4.39M of ammonium chloride and contained 9.1, 7.8 and 310 parts per million of Fe/Ca/Mg, respectively.

The second solution contained sodium chloride and 0.9% by weight of L-aspartic acid and 0.66% by weight of L-phenylalanine. Sodium hydroxide is used in the production of aspartame and is a valuable recyclable product. The second solution was analyzed and found to contain 4.07 molar sodium chloride and 3.9, 23 and 59 ppm of Fe, Ca and Mg, respectively, as major metallic impurities.

The isoelectric points of aspartic acid is reported to be at a pH of 2.98 and the isoelectric point of phenylalanine is reported to be at a pH of 5.91. This means that the operation with the waste stream pH controlled to the isoelectric points of both amino acids cannot be performed.

The two samples were aqueous solutions treated in a three compartment electrodialytic water-splitter of the type illustrated in FIG. 1.

FOR EXAMPLES 1 and 2

A four unit-cell electrodialytic water-splitting stack was assembled using bipolar membranes as taught in U.S. Pat. No. 4,766,161, cation membranes prepared according to U.S. Pat. No. 4,738,764 and anion membranes similar to the anion layer of the bipolar membrane. The active area of each membrane was 23 cm$^2$. The cell was assembled from the anode side as follows: anode 8 (nickel); electrode rinse compartment; 4 unit cells of bipolar membrane; acid compartment, anion membrane, salt compartment, cation membrane salt compartment; bipolar membrane electrode rinse compartment; and cathode (stainless steel).

Solutions for the electrode rinse, acid, salt and base were recirculated from reservoirs through the cell at 500 mL/min. The cell was operated at ambient tempratureture (about 35 degrees C.) at a current of 2.0A 2) The electrode rinse reservoir was charged (80A/ft$^2$). The electrode rinse reservoir was charged with 1L of 1M NaOH.

Acid and base current efficiencies were calculated based on the formula:

Efficiency = moles (acid or base) formed ÷ (number of cells × current (a) × time (sec) ÷ 96,500 (coul/mole))

Stack potential (volts) is the total applied potential (measured with a high impedance volt meter) including the potential needed for the electrode reactions.

EXAMPLE 1

The acid compartment was charged with 2.0L of 0.2N HCl, the base compartment with 0.9 L of 1N NaOH and the salt compartment with 500 mL of amino acid containing NaCl solution.

The pH of the salt feed to the salt compartment S was controlled at 3, close to the isoelectric point of the aspartic acid by adding 50% sodium hydroxide to the lt reservoir as needed. Results are summarized in Table 1.

Overall, 2.8N base and 1.1N acid were produced with about 75% current efficiency. The conductivity of the salt stream (Salt Cond). at the end of the experiment was 130,000 μS/cm (micro siemens per centimeter). The conductivity could have been reduced further, but insufficient volume remained in the salt reservoir to continue the run. During the experiment, the volume of salt decreased from about 410 mL to about 290 mL because of the water transport.

TABLE I

| Time (min) | Salt Cond. (S/cm) | Stack Potential (volts) | Temp. (deg. C.) | Concentration NaOH (moles/L) | HCl | Acid Eff. | Base Eff. |
|---|---|---|---|---|---|---|---|
| 0 | 0.210 | 11.81 | | | | | |
| 9 | | | | | 0.31 | | |
| 12 | | | | 1.23 | | | |
| 13 | | 13.06 | | | | | |
| 64 | | 12.44 | | | | | |
| 83 | | | | | 0.47 | 80% | |
| 87 | 0.210 | | 33 | 1.60 | | | |
| 100 | | 11.92 | | | | | |
| 174 | | 12.88 | | | | | |
| 180 | 0.195 | | 32 | | | | |
| 234 | | | | 2.18 | | 70% | |
| 239 | | | | | 0.74 | | |
| 242 | 0.185 | | 34 | | | | |
| 297 | 0.163 | 12.87 | 32 | | | | |
| 334 | | | | | | | |
| 339 | 0.150 | 13.32 | 32 | | | | |
| 402 | 0.130 | | | 2.82 | 1.06 | 77% | 74% |

EXAMPLE 2

For Example 2

Example 1 was repeated but the pH was maintained at 5, close to the isoelectric point of phenylalanine. 3.9 NaOH and 0.97 N HCl were produced with overall efficiency of about 70%.

The acid compartment was charged with 1000 mL of 0.1 N HCl, the base compartment with 200 mL of 0.1 N NaOH and the salt compartment with 200 mL of the NaCl/amino acid solution. The final salt volume was about 70 mL. During the interval from 9 min. to 108 min. The acid volume increased from 1000 mL to 1015 mL and the concentration from 0.160N to 0.535N. Thus, 0.383 moles of HCl were produced, a current efficiency of 78%.

In this experiment, the conductivity of the salt was reduced to 68,000 μS/cm and the volume decreased about 50%. The potential drop at 80ASF during most of the experiment was 11.2-11.5 volts at 34 deg and rose at the end to about 12.1 volts. Results are reported in Table 2 below.

TABLE 2

| Time (min) | Salt Cond. (S/cm) | Stack Potential (volts) | Temp. (deg. C.) | Concentration NaOH (moles/L) | HCl | Acid Eff. | Base Eff. |
|---|---|---|---|---|---|---|---|
| 0 | | 14.60 | | | | | |
| 9 | | | 29 | | 0.16 | | |
| 15 | | 12.63 | | 0.56 | | | |
| 19 | 0.200 | 11.93 | 31 | | | | |
| 41 | | 11.68 | 33 | | | | |
| 101 | | 11.53 | 33 | | | | |
| 104 | 0.170 | | | | | | |
| 108 | | | | | 0.54 | 78% | 78% |
| 111 | | | | 2.23 | | | |
| 113 | | 11.30 | 34 | | | | |
| 148 | | 11.21 | 34 | | | | |
| 181 | 0.120 | 11.21 | 35 | | | | |
| 204 | | 11.26 | 35 | | | | |
| 226 | | 12.12 | 35 | | | | |
| 244 | | 12.03 | 35 | | | | |
| 251 | 0.068 | 12.14 | | 3.88 | 0.97 | 64% | 62% |

In each case, most of the amino acids were retained in the product salt solution which was greatly reduced in salt content and suitable for recyle in the production process. The NH$_4$Cl solution was not treated.

EXAMPLE 3

An approximate mass balance for the process in FIG. 5 was calculated and is shown in Table 3. Process temperatures are near 45 degrees C except for the crystallizer 490, which is cooled to below 20 degrees C. to recover solid product in stream 422. GLY=glycine, GLYHCl=glycine hydrochloride, NaGLY=sodium glycinate.

TABLE 3

| | WEIGHT AMOUNTS (kg/day) | | | | | | | | | | | | |
|---|---|---|---|---|---|---|---|---|---|---|---|---|---|
| Stream | 401 | 402 | 403 | 406 | 407 | 408 | 409 | 410 | 411 | 412 | 413 | 415 | 416 |
| GLY | 7500 | 10500 | 3000 | 10297 | 5148.7 | 5148.7 | 0 | 0 | 0 | 0 | 0 | 0 | 0 |
| GLYHCl | 0 | 0 | 0 | 0 | 0 | 0 | 7574.4 | 6059.6 | 1514.9 | 6968.5 | 605.96 | 0 | 0 |
| NaGLY | 0 | 0 | 0 | 0 | 0 | 0 | 0 | 0 | 0 | 0 | 0 | 6592.4 | 1318.5 |
| HCl | 0 | 0 | 0 | 0 | 0 | 0 | 0 | 0 | 0 | 0 | 0 | 0 | 0 |
| NaOH | 0 | 0 | 0 | 0 | 0 | 0 | 0 | 0 | 0 | 0 | 0 | 0 | 0 |
| NaCl | 12275 | 16951 | 4676 | 9055 | 4527.5 | 4527.5 | 555.09 | 444.08 | 111.02 | 510.69 | 44.408 | 555.09 | 111.02 |
| H$_2$O | 72000 | 90210 | 18210 | 73190 | 36595 | 36595 | 31701 | 25361 | 6340.3 | 8982.7 | 22719 | 32925 | 6585 |
| Total | 91775 | 117661 | 25886 | 92542 | 46271 | 46271 | 39831 | 31865 | 7966.2 | 16462 | 23369 | 40072 | 8014.5 |
| Stream | 417 | 418 | 419 | 421 | 422 | 425 | 426 | 427 | 428 | 429 | 430 | 431 | 432 |
| GLY | 0 | 0 | 0 | 9378.9 | 6378.9 | 0 | 0 | 0 | 0 | 0 | 0 | 0 | 0 |
| GLYHCl | 0 | 0 | 0 | 0 | 0 | 0 | 0 | 0 | 0 | 0 | 150.55 | 0 | 76.51 |
| NaGLY | 5273.9 | 527.39 | 6065 | 0 | 0 | 0 | 0 | 0 | 0 | 131.03 | 0 | 66.59 | 0 |
| HCl | 0 | 0 | 0 | 0 | 0 | 0 | 0 | 0 | 0 | 0 | 4874.5 | 0 | 2452.2 |
| NaOH | 0 | 0 | 0 | 0 | 0 | 0 | 0 | 0 | 0 | 5349.2 | 0 | 2691 | 0 |
| NaCl | 444.08 | 44.408 | 510.69 | 4676 | 0 | 0 | 0 | 0 | 0 | 0 | 0 | 0 | 0 |

TABLE 3-continued

| | WEIGHT AMOUNTS (kg/day) | | | | | | | | | | | | |
|---|---|---|---|---|---|---|---|---|---|---|---|---|---|
| H₂O | 26340 | 23698 | 9227.4 | 18210 | 0 | 18350 | 36699 | 36471 | 72944 | 41359 | 82669 | 22032 | 40369 |
| Total | 32058 | 24259 | 15803 | 32265 | 6378.9 | 18350 | 36699 | 36471 | 72944 | 46839 | 87694 | 24790 | 42898 |

While exemplary embodiments of the invention have been described, the true scope of the invention is to be determined from the following claims.

What I claim is:

1. A process of separating at least two amphoteric compounds from an aqueous feed comprising the amphoteric compound and at least one salt, each salt comprising a salt anion and a salt cation, in an apparatus comprising at least one cell comprising at least one cation membrane, at least one anion membrane, and a bipolar membrane, the bipolar membrane comprising a cation layer and an anion layer, there being a base compartment between the anion layer of said bipolar membrane and the cation membrane, a salt compartment between said cation membrane and said anion membrane, and an acid compartment on the side of said anion membrane opposite the salt compartment comprising the steps of:
  supplying the feed to said salt compartment;
  supplying a liquid comprising water to said acid and base compartments;
  applying a direct current to the cell to force the salt cations to migrate to the base compartment to form base, and the salt anions to migrate to the acid compartment to form acid, the amphoteric compounds remaining in the salt compartment;
  recovering acid from the acid compartment;
  recovering base from the base compartment; and
  recovering an aqueous solution comprising the at least two amphoteric compounds from the salt compartment.

2. The process of claim 1 wherein the amphoteric compounds comprise at least two amino acids.

3. The process of claim 2 wherein said at least two amino acids are aspartic acid and phenylalanine.

4. The process of claim 2 wherein said at least two amino acids have different isoelectric points.

5. The process of claim 1 wherein the salt is sodium chloride.

6. The process as recited in claim 1 wherein the concentration of the feed stream is from 0.5 wt.% to 1.5 wt.% of aspartic acid, from 0.5 wt.% to 2 wt.% of phenylalanine, and from 10 wt.% to 25 wt.% sodium chloride.

7. A process of separating at least one amphoteric compound from an aqueous feed comprising the amphoteric compound and at least one salt, each salt comprising a salt anion and a salt cation, in an apparatus comprising at least one cell comprising at least one anion membrane, and a bipolar membrane, the bipolar membrane comprising a cation layer and an anion layer, there being a salt compartment between said anion layer of the bipolar membrane and the anion membrane, and an acid compartment on the side of said anion membrane opposite the salt compartment comprising the steps of:
  supplying the feed to said salt compartment;
  supplying a liquid comprising water to said acid compartment;
  applying a direct current to the cell to force the salt anions to migrate to the acid compartment to form acid, the salt cations and the amphoteric compound remaining in the salt compartment;
  recovering acid from the acid compartment; and
  recovering an aqueous solution comprising basified amphoteric compound from the salt compartment.

8. The process of claim 7 wherein the amphoteric compound comprises at least one amino acid.

9. The process of claim 8 wherein said amino acid is a mixture of aspartic acid and phenylalanine.

10. The process of claim 7 wherein the salt is sodium chloride.

11. The process as recited in claim 7 wherein the concentration of the feed stream is from 0.5 wt.% to 1.5 wt.% of aspartic acid, from 0.5 wt.% to 2 wt.% of phenylalanine, and from 10 wt.% to 25 wt.% sodium chloride.

12. A process of separating at least one amphoteric compound from an aqueous feed comprising the amphoteric compound and at least one salt, each salt comprising a salt anion and a salt cation, in an apparatus comprising at least one cell comprising at least one cation membrane and a bipolar membrane, the bipolar membrane comprising a cation layer and an anion layer, there being a salt compartment between said cation layer of the bipolar membrane and the cation membrane, and a base compartment on the side of said cation membrane opposite the salt compartment comprising the steps of:
  supplying the feed to said salt compartment;
  supplying a liquid comprising water to said base compartment;
  applying a direct current to the cell to force the salt cations to migrate to the base compartment to form base, the salt anions and the amphoteric compound remaining in the salt compartment;
  recovering base from the base compartment; and
  recovering an aqueous solution comprising acidified amphoteric compound from the salt compartment.

13. A process of separating at least one amphoteric compound from an aqueous feed comprising the amphoteric compound and at least one salt, each salt comprising a salt anion and a salt cation, in an apparatus comprising at least one cell comprising at least one cation membrane, at least one anion membrane, and at least two bipolar membranes, each bipolar membrane comprising a cation layer and an anion layer, there being a salt compartment between said cation layer of the first bipolar membrane and the cation membrane, a base compartment between the cation membrane and the anion layer of the second bipolar membrane, an acid compartment formed by the cation layer of the second bipolar membrane and the anion membrane and a second salt compartment on the side of the anion membrane opposite the acid compartment comprising the steps of:
  supplying the feed to said first and second salt compartment;
  supplying a liquid comprising water to said acid and base compartments;
  applying a direct current to the cell to force the salt cations to migrate from the first salt compartment to the base compartment to form base, and the salt anions to migrate from the second salt compartment to the acid compartment to form acid, amphoteric compound and salt anions remaining in the first salt compartment, and amphoteric compound and salt cations remaining in the second salt compartment;

recovering acid from the acid compartment;

recovering base from the base compartment; and recovering an aqueous solution comprising acidified amphoteric compound from the first salt compartment, and basified amphoteric compound from the second salt compartment.

14. The process of claim 13 wherein the amphoteric compound comprises at least one amino acid.

15. The process of claim 14 wherein said amino acid is a mixture of aspartic acid and phenylalanine.

16. The process of claim 13 wherein the salt is sodium chloride.

17. The process as recited in claim 13 wherein the concentration of the feed stream is from 0.5 wt.% to 1.5 wt.% of aspartic acid, from 0.5 wt.% to 2 wt.% of phenylalanine, and from 10 wt.% to 25 wt.% sodium chloride.

18. The process of claim 2 further comprising the step of concentrating the aqueous solution of salt and amphoteric compound prior to supplying the feed to the salt compartment.

19. The process of claim 18 wherein the step of concentrating is conducted in an electrodialytic cell.

* * * * *